United States Patent [19]

Hirohara et al.

[11] 4,247,642
[45] Jan. 27, 1981

[54] ENZYME IMMOBILIZATION WITH PULLULAN GEL

[75] Inventors: Hideo Hirohara; Shigeyasu Nabeshima; Masanori Fujimoto, all of Ibaraki; Tsuneyuki Nagase, Takatsuki, all of Japan

[73] Assignee: Sumitomo Chemical Company, Limited, Osaka, Japan

[21] Appl. No.: 878,572

[22] Filed: Feb. 16, 1978

[30] Foreign Application Priority Data

Feb. 17, 1977 [JP] Japan ............................... 52-16835
Aug. 26, 1977 [JP] Japan ............................. 52-102999

[51] Int. Cl.$^3$ ............................................. C12N 11/10
[52] U.S. Cl. ................................... 435/178; 435/180; 435/181
[58] Field of Search ................... 195/63, 68, DIG. 11; 536/52, 1; 435/174, 177, 178, 181

[56] References Cited

U.S. PATENT DOCUMENTS

| 3,645,852 | 2/1972 | Axen et al. | 195/63 X |
| 3,905,954 | 9/1975 | Jones et al. | 195/63 X |
| 4,090,022 | 5/1978 | Tsao et al. | 195/63 X |
| 4,152,170 | 5/1979 | Nagase et al. | 536/1 X |

Primary Examiner—David M. Naff
Attorney, Agent, or Firm—Stevens, Davis, Miller & Mosher

[57] ABSTRACT

Enzymes are immobilized by a process wherein the carrier used for immobilizing is a hydrophilic pullulan gel having a three-dimensionally reticulated structure obtained by the reaction between pullulan and a bifunctional compound capable of forming an ether linkage with the hydroxyl group contained in the glucose unit of pullulan, or an ionic pullulan gel obtained by the reaction between said hydrophilic pullulan gel and a compound having at one end an ionizable group and at the other end a functional group capable of forming an ether linkage with the hydroxyl group in the pullulan gel in the presence of an alkaline coumpound. Immobilized enzymes prepared according to this process have a high activity and good retention of the activity.

25 Claims, No Drawings

ENZYME IMMOBILIZATION WITH PULLULAN GEL

This invention relates to an immobilized enzyme and a process for immobilizing an enzyme. More particularly, it relates to a process for preparing an immobilized enzyme, characterized by using a pullulan gel or its ionic derivative as an immobilizing carrier.

Examples of polysaccharides containing glucose units in their molecules which have been known to be utilizable as an enzyme-immobilizing carrier are cellulose gels and dextran gels. The agarose gel has also been utilized as a similar carrier. The cellulosic material, however, tends to pass into the reaction solution by solubilization during continuous use and, hence, lacks durability; it is also difficult to immobilize a large amount of enzyme per unit weight of the cellulosic carrier. Although a cross-linked dextran (dextran gel) and an agarose gel can immobilize a relatively large amount of enzyme per unit weight, yet it is difficult to obtain directly these materials having a desired degree of polymerization. For this reason, the dextran gel and agarose gel are very expensive so that there results a great economical burden to employ these materials as enzyme-immobilizing carriers on a commercial scale.

Considering the above-noted problems, the present inventors conducted extensive studies and, as the result, have found that an immobilized enzyme having a high activity and excellent properties can be obtained by using as the carrier a hydrophilic gel prepared by crosslinking pullulan which is controllable to have a desired molecular weight in its production and has a number of excellent characteristics, or by using ionic pullulan gel as the carrier.

An object of this invention is to provide a simple process for preparing an immobilized enzyme which is stable and of high enzymatic activity.

Another object of this invention is to provide a process for preparing an immobilized enzyme which can be utilized in such an efficient way that it permits of an enzymatically catalyzed continuous reaction of the substrate by removing the reacting solution from the immobilized enzyme, the reaction ceases to proceed.

Other objects and advantages of this invention will become apparent from the following description.

Pullulan used in this invention is a linear polymer in which maltotriose (a trimer of glucose) units are recurrently arranged through α-1,6-linkages which are different from the linkages in said trimer. A hydrophilic gel of a three-dimensionally reticulated structure is obtained by the reaction of pullulan with a bifunctional compound capable of forming ether linkages, whereby the reactivity of hydroxyl groups in the glucose units is utilized to advantage. Further, an ionic pullulan gel is produced by the reaction of the above-mentioned hydrophilic gel with a compound having at one terminal of its molecule an ionizable group and at the other a functional group capable of forming an ether linkage with the hydroxyl group in the glucose unit in the presence of an alkaline compound. Although pullulan is composed of glucose units, pullulan is different entirely in molecular structure and markedly in properties from conventionally known polysaccharides such as, for example, starch and derivatives thereof or cellulose and derivatives thereof. Pullulan has many desirable properties. For instance, it is readily soluble in cold as well as hot water, forming an aqueous solution which has a low viscosity and is more stable for a long period of time without being subjected to gelation or aging, as compared with the aqueous solutions of other polysaccharides; pullulan itself is non-toxic and has a desirable affinity for biological materials.

The procedures of producing a pullulan-based hydrophilic gel and a pullulan-based ionic gel which are used in this invention are described below.

Firstly, the hydrophilic gel is obtained, as already disclosed in German Patent Application Laid-open (DT-OS) No. 2,627,125 corresponding to U.S. Patent Application Ser. No. 695,762, filed June 14, 1976, and now U.S. Pat. No. 4,152,170, by crosslinking pullulan by using as the crosslinking agent a bifunctional compound represented by the formula

wherein X and Z are each a halogen atom or an epoxy group and Y is an aliphatic residue having 1 to 30, preferably 1 to 6 carbon atoms, which may be substituted by oxygen atoms. Although there is no limit for the molecular weight of pullulan, an average molecular weight of $1 \times 10^4$ to $1 \times 10^6$ is preferred.

Examples of suitable bifunctional compounds include epichlorohydrin, epibromohydrin, dichlorohydrin, dibromohydrin, ethylene glycol diglycidyl ether, triethylene glycol diglycidyl ether, diglycidyl ether, and 1,6-hexanediol diglycidyl ether.

The crosslinking reaction for producing the hydrophilic gel is carried out in an aqueous solution or a mixed solvent comprising water and an alcohol, or water and acetone in the presence of an alkaline substance such as, for example, sodium hydroxide, potassium hydroxide or calcium hydroxide, usually at a temperature in the range of 10° C. to 70° C. for 1 to 24 hours, preferably 2 to 10 hours. Under otherwise the same conditions, with a decrease in amount of the solvent, with an increase in the molecular weight of pullulan, and with an increase in the amount of the bifunctional compound, the degree of crosslinking becomes larger, that is, harder beads are formed.

The hardness of the hydrophilic bead or the water regain of the bead is preferably in the range of 1 to 50 g/g of dry beads, because a bead with too large a water regain is mechanically weak, whereas if the water regain of the bead is extremely small, the meshes of the network or the pore size is too small and, in addition, the number of hydroxyl groups available for immobilization of an enzyme becomes small.

A hydrophilic gel in spherical bead form is desirable as the enzyme-immobilizing carrier. Such a gel is obtained usually by dispersing an aqueous solution containing 20 to 60% by weight of pullulan in a liquid dispersion medium (for example, n-hexane, heptane, isooctane, benzene or toluene) which is immiscible with the aqueous solution and contains a dispersion stabilizer such as polyvinyl acetate or the like to form a two-phase dispersion system containing said aqueous solution in the form of droplets, and allowing the dispersion to react while being stirred at a controlled rpm. The particle size of the gel thus formed can be empirically predetermined. However, since the particle size has generally a certain distribution, the product is screened if desired. Spherical beads having a diameter of 10 to 500μ are preferred for the enzyme-immobilizing carrier.

As for the type of attachment of an enzyme with the hydrophilic gel obtained above, all of the various attachment techniques utilizing the reactivity of hydroxyl group contained in the glucose unit or, in some cases, in the bifunctional compound can be adopted. Of the various techniques, those particularly preferred producing an immobilized enzyme having a high activity and good retention of the activity are (1) attachment by means of a triazinyl derivative using cyanuric chloride, (2) attachment by means of azide linkage, (3) attachment by means of diazo linkage, (4) attachment by means of a monohalogenacetyl derivative, and (5) attachment by the reaction with a chloride of titanium, tin, zirconium, vanadium or iron.

Next, the procedure for the preparation of an ionic pullulan gel is described below.

It is desirable that the ionic pullulan gel for use as the enzyme-immobilizing carrier have "hardness", that is, a water regain of 1 to 50 g/g of dry gel and a spheric form of 10 to 500µ in diameter. Such an ionic pullulan gel is obtained by reacting in the presence of an alkaline substance the aforementioned hydrophilic pullulan gel with a compound represented by the formula

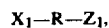  (A)

wherein $X_1$ is a halogen or

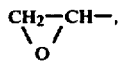

R is a linear alkyl group having 1 to 4 carbon atoms, which may have a hydroxyl group as a substituent, and $Z_1$ is a carboxyl group, phosphoric acid group, sulfonic acid group, guanidino group,

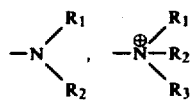

(where $R_1$, $R_2$ and $R_3$ are each hydrogen, methyl group, ethyl group, hydroxyethyl group, hydroxypropyl group or phenyl group), or a salt of these compounds; or a compound represented by the formula

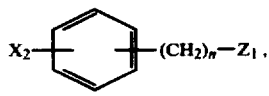  (B)

wherein $X_2$ is Hal—$(CH_2)_m$— (where Hal means halogen, and m is an integer of 1 to 3), or

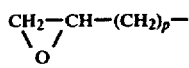

(where p is an integer of 1 to 3), n is an integer of 0 to 3, and $Z_1$ is as defined above or a salt of these compounds; or a compound represented by the formula

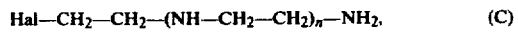  (C)

wherein n is an integer of 0 to 3 and Hal means halogen or a salt thereof.

Although the hydrophilic pullulan gel to be used in preparing the ionic pullulan gel is not limited in its water regain, a suitable water regain per g of dry hydrophilic gel is in the range of 1 to 50 g/g, preferably 1 to 30 g/g. It is also preferred that the hydrophilic pullulan gel be in the form of spherical bead having 10 to 500µ in diameter.

The suitable compounds to be reacted with the hydrophilic pullulan gel include amino compounds such as 2-dimethylaminoethyl chloride, 2-diethylaminoethyl chloride, 2-dimethylaminoisopropyl chloride, 2-bromo-5-diethylaminopentane, 2-diphenylaminoethyl chloride, 3-(N,N-dimethylphenylamino)ethyl chloride, 3-amino-1,2-epoxypropane, 3-dimethylamino-1,2-epoxypropane, 3-diethylamino-1,2-epoxypropane, 3-dibutylamino-1,2-epoxypropane, 3-diphenylamino-1,2-epoxypropane (all of these compounds are categorized in formula (A)), 3-(N,N-dimethylphenylamino)-1,2-epoxypropane, N,N-(2,3-epoxypropyl)methylaniline (these two compounds are categorized in formula (B)), 2-chloroethylamine (categorized in formula (C)), and salts thereof; and include carboxylic acid compounds such as chloroacetic acid, bromoacetic acid, chloropropionic acid, and salts thereof; and sulfonic acids such as chloromethanesulfonic acid, bromoethanesulfonic acid, chloroethanesulfonic acid, and salts thereof (all of these acids compounds are categorized in formula (A)).

The above-noted compounds are used in an amount in excess of the stoichiometric amount in order to promote the reaction. It is desirable to use 1/30 to 10 moles, preferably 1/10 to 5 moles of the above compounds per mole of the glucose unit in pullulan.

The alkaline substances used in reacting the hydrophilic pullulan gel with the above-noted compound include alkali metal hydroxides such as sodium hydroxide and potassium hydroxide, alkali earth metal hydroxides such as calcium hydroxide and magnesium hydroxide, and, in some cases, organic amines such as ethylenediamine, diethylenetriamine and triethylamine. Of these compounds, sodium hydroxide is most preferred. The amount to be added of the alkaline substance is generally 0.1 to 10 times as much as the moles of the aforementioned compound to be reacted with the hydrophilic pullulan gel. However, in the case where a hydrogen halide is liberated during the reaction, it is necessary to use the alkaline substance in an amount sufficient for neutralization.

As for the reaction solvent, there is no special limitation so long as it does not adversely affect the reaction. Suitable solvents are water, dimethyl sulfoxide, N,N-dimethylformamide, N,N-dimethylacetamide, benzene, toluene, chloroform, and ethyl acetate. Of these solvents, water is preferred.

The reaction conditions are also not particularly restricted. Although a reaction temperature below 200° C. is generally suitable, undesirable side reactions would take place in some cases at a temperature exceeding 100° C. Therefore, a reaction temperature of 5° to 100° C. is more desirable.

The coupling of an enzyme with the ionic pullulan gel carrier thus prepared can be effected by either the ionic adsorption method or the covalent attachement method.

In the case of the ionic adsorption method, a cationic or an anionic pullulan gel is selected as the carrier by taking into account the relation between the isoelectric point and the optimal pH of action of the enzyme being immobilized. For instance, in immobilizing an enzyme of the acidic protein type having an isoelectric point at around pH 5 and an optimal pH of about 7, it is desirable to use as the carrier a cationic pullulan gel such as diethylaminoethylated pullulan gel, while in the case of an enzyme of the basic protein type having its isoelectric point at around pH 10 and active in an approximately neutral condition it is desirable to use an anionic pullulan gel such as carboxymethylated pullulan gel as the carrier.

Thus, in the first step of the preparation of an immobilized enzyme by the ionic adsorption method, an ionic pullulan gel is treated in a conventional way with, for example, about 0.02 to 1 molar solution of hydrochloric acid or sodium hydroxide to activate the ion exchange group or the ionic pullulan gel is adjusted to the optimal pH of the enzyme being immobilized by use of an appropriate buffer solution (0.02 to 1 molar solution). Then, in the next step, the thus treated ionic gel is immersed in a solution containing an enzyme being immobilized for a sufficient period of time and, if necessary, stirred to obtain the final product after filtration and washing. The temperature at which the enzyme is adsorbed and immobilized is preferably 0° C. to 40° C., most preferably about 4° C. The preferred adsorption time is 1 hour to 24 hours. The immobilized enzyme thus obtained contains, in general, about 100 mg or less of the enzyme protein per g of dry carrier. The product is highly active and is stable unless washed with a salt solution of high ionic strength.

As far the covalent attachment method, it was found that an immobilized enzyme with high activity and good retention of activity is obtained by adopting any of those various attachment methods which utilize the reactivity of either the hydroxyl group originally present in the pullulan gel or a later introduced ionic group such as primary amino group, secondary amino group or carboxyl group. Such methods have already been proved to be effectively applicable to the preparation of ionic cellulose or ionic dextran gel.

Particularly favorable methods which utilize the reactivity of the hydroxyl group originally present in the pullulan gel or an ionic group later introduced into the gel such as primary amino group, secondary amino group or carboxyl group in immobilizing an enzyme include (1) attachment by means of triazinyl derivative by use of cyanuric chloride, (2) attachment through an azide linkage, (3) attachment by means of diazo linkage, (4) attachment by means of a monohalogenacetyl derivative, (5) attachment by use of carbodiimide derivative, and (6) attachment by use of glutaraldehyde. Although more complicated to carry out, the covalent attachment method generally gives an immobilized enzyme more stable than the one prepared by the ionic adsorption method.

The enzymes which can be immobilized by the methods of this invention have no particular limitation in their types, except for those which are completely deprived of their activities on being immobilized by the present attachment methods. Examples of enzymes which can be successfully immobilized are trypsin, chymotrypsin, lipase, microbial protease, esterase, cholinesterase, urease, bromelain, ribonuclease, deoxyribonuclease, penicillinamidase, aminoacylase, $\beta$-galactosidase, glucose isomerase, glucose oxidase, creatinekinase, peroxidase, papain, invertase, pepsin, $\beta$-amylase, isoamylase, maltase and uricase.

The invention is illustrated below in further detail with reference to Examples which are merely illustrative and not limitative since many modifications may be made without departing from the nature and principle of this invention. In Examples all parts are by weight.

EXAMPLE 1

40 Parts of pullulan having an average molecular weight of 72,000 were dissolved in 80 parts of water and admixed with 12.5 g of sodium hydroxide to form a uniform aqueous solution. This solution was added to a dispersion medium containing 10 parts of polyvinyl acetate, 160 parts of toluene and 1.2 parts of sorbitan monostearate. The mixture was stirred at 800 rpm to disperse said aqueous solution in the form of droplet. After one hour from the time of addition of the aqueous solution, 29 parts of epichlorohydrin were added to the dispersion and allowed to react at 50° C. for 5 hours. The reaction product was filtered and washed by using toluene and methanol, successively, and dried in vacuo to obtain a hydrophilic pullulan gel in spherical bead form having a water regain of 2.35 g/g. 100 Parts of this pullulan gel were dispersed in 480 parts of an aqueous solution containing 110 parts of sodium hydroxide. To the resulting dispersion, while being stirred at room temperature (about 20° C.), were added dropwisely 240 parts of a solution of 2-diethylaminoethyl chloride hydrochloride dissolved in 220 parts of water over a period of 4 hours. After completion of the dropwise addition, the reaction was continued for a further 14 hours. The reaction product was washed with water and methanol to obtain diethylaminoethylated pullulan gel (DEAE-pullulan gel) in spherical bead form, 37 to 149$\mu$ in diameter in dry condition, having a water regain of 2.8 g/g and an amine content of 2.7 meq/g, as measured by conductometric titration. By using as a carrier the DEAE-pullulan gel thus obtained, a commercial enzyme, Pronase E, was immobilized by the ionic adsorption method as described below.

1 Gram (dry basis) of the DEAE-pullulan gel was treated with 0.1 N sodium hydroxide solution and then thoroughly washed with water to remove excess sodium hydroxide. The resulting activated DEAE-pullulan gel was added to 20 ml of a 0.02 M (M stands for "molarity", the same applies hereinafter) phosphate buffer solution of pH 7.0 and containing 50 mg of the commercial Pronase E (produced by Kaken Chemical Co.) dissolved therein. The enzyme was allowed to be adsorbed on the DEAE-pullulan gel at 4° C. for a period of 5 hours with gentle stirring. The DEAE-pullulan gel thus treated was collected by filtration with a glass filter under application of suction, and then thoroughly washed with 0.02 M phosphate buffer solution (pH 7.0) and water. The filtrate and the washings were combined into a recovered solution. From the measurement of the ultraviolet absorption intensity at 280 nm of the recovered solution, it was found that the amount of enzyme immobilized by adsorption on the DEAE-pullulan gel was 39 mg. The specific activity of the immobilized enzyme was assayed at 30° C. and pH 7.0 by means of a pH-stat (Hiranuma pH-stat PS-11) using N-benzoyl-L-alginine ethyl ester (BAEE) as substrate and found to be 3.2 $\mu$moles/mg.min. under the condition of excess substrate for the amount of enzyme. This activity corresponded to 35% of that of the enzyme in the solution prior to immobilization. The activity of the immobilized enzyme was repeatedly assayed 5 times under the same conditions as given above. The activity in the fifth run was found to be about 73% of that in the first run.

EXAMPLE 2

70 Milligrams of an enzyme, Pronase E (produced by Kaken Chemical Co.), were dissolved in 25 ml of 0.05 M phosphate buffer solution (pH 6.0) maintained at 4° C. To the resulting solution, was added 1.0 g (dry basis) of DEAE-pullulan gel having the same properties as those of the gel used in Example 1. While being slowly stirred, the mixture was kept at about 4° C. to immobilize the enzyme. The immobilized Pronase E was washed successively with 0.05 M phosphate buffer solution (pH 6.5), 0.1 M sodium chloride solution and purified water until no optical absorption due to the protein was detected in the washing. The washings were combined as a recovered solution. On measurement of the intensity of ultraviolet absorption of the recovered solution due to the protein, the amount of immobilized enzyme was found to be 49 mg. The specific activity of the immobilized enzyme was assayed at 40° C. and pH 6.0 by means of a pH-stat using DL-lysine methyl ester as substrate and found to be 37% of that of the enzyme in the solution prior to immobilization.

EXAMPLE 3

100 Milligrams of commercial papain (obtained from Nakarai Chemical Co.) were dissolved in 30 ml of 0.02 M phosphate buffer solution (pH 6.0) maintained at 4° C. to prepare papain solution.

A hydrophilic pullulan gel in spherical bead form having a water regain of 2.5 g/g was prepared in the same manner as in Example 1 using the same materials and the same reaction conditions, except that 24.5 parts of epichlorohydrin were used. A solution containing 30 parts of the above hydrophilic pullulan gel, 30 parts of monochloroacetic acid and 20 parts of water was stirred in 200 parts of methanol at 10° C. for 6 hours to prepare a carboxymethylpullulan gel (CM-pullulan gel) in spherical bead form, 74 to 149μ in diameter in dry condition, having a water regain of 2.9 g/g and a carboxyl group content of 3.1 meq/g, as measured by conductometric titration. 1.0 Gram of the CM-pullulane gel was added to the aforementioned papain solution and, while maintaining at about 4° C., slowly stirred to immobilize the enzyme. The immobilized enzyme was washed in the same manner as in Example 2. From the measurement of the amount of protein in the recovered solution by Lowry's method, the amount of the immobilized enzyme was found to be 30.1 mg. The specific activity of the immobilized enzyme was assayed at 40° C. and pH 6.2 by means of a pH-stat using BAEE as substrate and found to be 1.70 μmoles/mg.min. corresponding to 23% of that of the enzyme in the solution prior to immobilization. In assaying the specific activities of immobilized enzyme and that of the enzyme in solution prior to immobiliation, ethylenediaminetetraacetic acid, cystein, and sodium chloride in $2 \times 10^{-3}$, $5 \times 10^{-3}$ and 0.15 molar concentration, respectively, were present.

EXAMPLE 4

50 Milligrams of commercial purified trypsin (obtained from Sigma Chemical Co.) were dissolved in 30 ml of a 0.02 M Tris-hydrochloric acid buffer solution (containing calcium chloride in 0.02 molar concentration) kept at 4° C. To the resulting solution, was added 1.0 g of the CM-pullulan gel used in Example 3 and the mixture was slowly stirred for about 3 hours, while being maintained at about 4° C., to immobilize the enzyme. From the ultraviolet absorption intensity of the protein in the recovered solution, the amount of immobilized enzyme was found to be 22 mg. The specific activity of the immobilized enzyme was assayed by means of a pH-stat at 30° C. and pH 7.5 in the presence of calcium chloride in 0.02 molar concentration and found to be 5.5 μmoles/mg.min., corresponding to 21% of that of the enzyme in the solution prior to immobilization.

EXAMPLE 5

A glucose isomerase having an activity of 7,500 units and a protein content of 84 mg by Lowry's method, was dissolved in 25 ml of a 0.05 M phosphate buffer solution at pH 7.5 to prepare an enzyme solution. The said glucose isomerase preparation had been carried out by grounding living cells of *Streptomyces phaeochromogenes*, refrigerated centrifugation and purifying the supernatant by the method of acetone precipitation.

A DEAE-pullulan gel in spherical bead form, 39 to 149μ in diameter in dry condition, having a water regain of 3.0 g/g and a diethylaminoethyl (DEAE) group content of 2.5 meq/g, as measured by conductometric titration, was prepared by soaking and dispersing 32 g of the hydrophilic pullulan gel prepared in Example 3 in an alkaline solution containing 35 parts of sodium hydroxide and 150 parts of water, adding dropwisely 68 parts of 2-diethylaminoethyl chloride hydrochloride dissolved in 40 parts of water to the resulting dispersion, and allowing the reaction to proceed at room temperature for 18 hours. 3.0 Grams of the DEAE-pullulan gel thus prepared were added to the aforementioned enzyme solution and the mixture was shaken at 60 rpm for 10 hours, while maintaining the temperature at about 15° C., to immobilize the enzyme on the gel. After completion of the immobilization, the immobilized enzyme was collected by filtration and washed throughly with a 0.05 M phosphate buffer solution at pH 7.5. From the assay of the activity and protein content of the filtrate, the immobilized activity and the amount of immobilized protein were found to be 6,980 units and 71 mg, respectively.

The immobilized glucose isomerase thus obtained was packed in a jacketed column, 1.0 mm in diameter and, while maintaining the jacket temperature at 60° C., a 54% (W/V) aqueous solution of crystalline glucose (containing $Mg^{++}$ ion in a $5 \times 10^{-3}$ molar concentration; adjusted to pH 7.5) was passed from the top of the column downward by means of a pump to perform isomerization. The flow rate (space velocity) was kept at 2 $hr^{-1}$ and the column was run uninterruptedly day and night. The conversion to fructose was constantly 51.5% during about 350 hours after the beginning of the reaction and thence decreased slowly. The half-life was about 50 days.

Note 1. One unit of glucose isomerase is the amount of enzyme capable of producing 1 mg/hour of fructose, when isomerization is carried out using 0.1 M D-glucose as substrate in the presence of 0.05 M phosphate buffer and 0.005 M phosphate buffer and 0.005 M $MgSO_4.7H_2O$ at 70° C. and pH 7.0 for one hour.

Note 2. Quantitative determination of fructose was conducted by the cystein-carbazole-sulfuric acid method as specified in Japanese Agricultural Standard (JAS).

In the following Examples, the unit of the glucose isomerase and the quantity of fructose were determined in the same manner as described above.

EXAMPLE 6

Glucose isomerase having an activity of 7,600 units and a protein content of 70 mg, which had been purified in the same manner as in Example 5, was dissolved in 25 ml of a 0.05 M phosphate buffer solution at pH 7.65 to prepare an enzyme solution.

10 Parts of the hydrophilic pullulan gel prepared in Example 3 were added to 100 parts of an alkaline aqueous solution of β, γ-epoxypropyltriethylammonium chloride obtained by the epoxidation of 30 parts of γ-chloro-β-hydroxypropyltrimethylammonium chloride with 6 parts of sodium hydroxide to prepare β-hydroxypropyltrimethylaminopullulan gel in spherical bead form, 39 to 149μ in diameter in dry condition, having a water regain of 2.8 g/g and a β-hydroxypropyltrimethylamino (β-HPTMA) group content of 0.57 meq/g, as determined by conductometric titration. 3.0 Grams of the β-HPTMA-pullulan gel were added to the aforementioned enzyme solution. While being heated at 15° to 20° C., the mixture was shaken for 10 hours at 80 rpm to immobilize the enzyme. After completion of the immobilization, the immobilized enzyme was washed as in Example 5. It was found from the assay of the recovered washings that the immobilized activity was 7,110 units and the amount of immobilized protein was 65 mg.

The immobilized glucose isomerase thus prepared was packed in a jacketed column, 1.5 mm in diameter and, while maintaining the jacket temperature at 65° C., a 54% (W/V) aqueous solution of crystalline glucose (containing $5 \times 10^{-3}$ M $MgSO_4.7H_2O$ and adjusted to pH 7.65) was passed from the top of the column downward by means of a pump at a space velocity of 2 $hr^{-1}$ to perform continuous isomerization. The conversion remained constantly at 53.5% over a period of 350 hours from the beginning of the reaction.

EXAMPLE 7

100 Milligrams of β-galactosidase, which had been obtained as an extracellular enzyme of *Aspergillus oryzae* and purified by the method of alcohol precipitation, were dissolved in 25 ml of 0.02 M citrate-phosphate buffer solution at pH 5.5 to prepare enzyme solution. To the solution was added 1.0 g of the same DEAE-pullulan gel as used in Example 5. While maintaining the temperature at about 4° C., the mixture was shaken at 60 rpm for 10 hours to immobilize the enzyme on the gel. After completion of the immobilization, the immobilized enzyme was washed with 0.02 M citrate-phosphate buffer solution (pH 5.5) and purified water until the protein was no more detected in the washing. From the ultraviolet absorption intensity of protein in the recovered solution, the amount of immobilized enzyme was found to be 40 mg. The determination by Lowry's method also showed that 43 mg of the enzyme was immobilized. The specific activity of the immobilized enzyme was assayed at 30° C. and pH 4.5 using 5% (W/V) lactose solution as substrate and found to be 1.70 μmoles/mg.min. The activity was assayed by the colorimetric determination of the amount of glucose produced by use of a reagent comprising glucose oxidase-peroxidase-dye mixture which reacts with glucose.

EXAMPLE 8

2 Grams of the same DEAE-pullulan gel as used in Example 1 were immersed in 25 ml of 1 N sodium hydroxide solution and stirred for 15 minutes at room temperature (about 20° C.). After removing the excess alkali solution by filtration, the DEAE-pullulan gel thus treated was immersed in 25 ml of dioxane for 5 minutes at room temperature. Then, 20 ml of a dioxane solution containing 4 g of cyanuric chloride were added to the gel and the mixture was stirred at room temperature. After one minute, to the mixture were added 25 ml of ice-cooled water followed by 25 ml of acetic acid to terminate the reaction. After filtration of the solution, the resulting s-triazinyl DEAE-pullulan gel was quickly washed with cold acetone and ice-cooled water and immediately subjected to the succeeding immobilization treatment which was carried out in the following way.

The above s-triazinyl DEAE-pullulan gel was added to a solution containing 170 mg of Pronase E dissolved in 20 ml of a phosphate buffer solution, which had been kept at 4° C. and pH 8.0, and the resulting mixture was stirred for 5 hours while keeping the pH at 8.0 by the addition of 0.2 N sodium hydroxide solution and controlling the temperature so as not to exceed 4° C. After 5 hours of reaction, the immobilized enzyme was collected by filtration and washed with a 5 M sodium chloride solution, 0.1 M phosphate buffer solution (pH 6.0) and cold water until no protein had been detected in the washing. The washings were recovered. From the intensity of the ultraviolet absorption at 280 nm of the recovered solution, the amount of immobilized enzyme was found to be 66 mg per g of dry gel. The specific activity of the immobilized enzyme thus prepared was assayed by means of a pH-stat by using a 20% (weight) solution of DL-lysine methyl ester as substrate solution at 30° C. and pH 6.0, and found to be 2.94 μmoles/mg.min. which corresponded to 60% of the specific activity of the enzyme in the solution prior to immobilization.

EXAMPLE 9

1.0 Gram of the DEAE-pullulan gel having the same properties as those of the gel used in Example 1 was immersed in 35 ml of water. After addition of 1.0 g of cyanogen bromide, while keeping the temperature at 4° C. with stirring, 5 N sodium hydroxide solution was added dropwise so as to keep at pH 11.0. When no further decrease in pH had been observed, the gel was separated by filtration and quickly washed with 0.1 M borate buffer solution (pH 8.0). The DEAE-pullulan gel thus activated with the cyanogen bromide was transferred into 10 ml of 0.1 M borate buffer solution (pH 8.0) containing 80 mg of Pronase E and stirred for 2 hours with gentle reciprocate movement to immobilize the Pronase E. In order to deactivate the unreacted active groups, the resulting gel of immobilized pronase was washed with 10 times its volume of water and then immersed in 1.0 M ethanolamine solution (pH 8.0). After having been stirred for 2 hours at room temperature (about 20° C.), the gel of immobilized enzyme was separated by filtration and washed repeatedly with 0.1 M acetate buffer solution (pH 4.0) containing 1 mole/liter of sodium chloride, 0.1 M borate buffer solution (pH 8.0) containing 1 mole/liter of sodium chloride, and cold water. The washings were recovered. From the intensity of ultraviolet absorption at 280 nm in the recovered solution, the amount of immobilized enzyme was found to be 31 mg per g of dry gel by calculation. The specific activity of the immobilized enzyme was assayed by means of a pH-stat using DL-lysine methyl ester as substrate at 40° C., pH 6.0, and a substrate concentration of 20% (weight) and found to be 3.12 μmoles/mg.min., corresponding to 52% of the specific activity of the enzyme in the solution prior to immobilization.

EXAMPLE 10

Under the same conditions as in Example 8, 2.0 g of the β-HPTMA-pullulan gel having exactly the same properties as those of the gel used in Example 6 were reacted with cyanuric chloride and washed to prepare s-triazinyl β-HPTMA-pullulan gel. The gel thus obtained was added to 25 ml of 0.05 M phosphate buffer solution containing 60 mg of a glucose isomerase (110 units/mg) obtained from *Streptomyces phaeochromogenes*. The immobilization and washing procedure was the same as in Example 8. The activity of the resulting immobilized enzyme was assayed by shaking the gel in 50 ml of 0.05 M phosphate buffer solution (pH 7.65 and containing 0.005 mole/liter of $Mg^{++}$ ion) containing 0.1 mole/liter of glucose, at 70° C. for one hour and it was found that the immobilized enzyme was 6,270 units. The immobilized enzyme was packed in a jacketed column, 12 mm in diameter. While circulating hot water at 60° C. through the jacket, 54% (W/V) (3 moles/liter) solution of crystalline glucose (pH 7.5; containing 0.005 mole/liter of $Mg^{++}$ ion) was passed through the column at a space velocity of $3.0 \, hr^{-1}$. On determining the fructose content of the effluent by the method of cysteincarbazole-sulfuric acid, it was found that the conversion of glucose to fructose was 52%.

EXAMPLE 11

2 Grams of the same CM-pullulan gel as used in Example 3 was immersed in 40 ml of methanol and converted in a conventional manner to its methyl ester using gaseous hydrogen chloride. The methyl ester was reacted with hydrazine hydrate to yield a hydrazide which was further converted to an azide by using 3% sodium nitrite solution. The resulting azide was immediately immersed in 25 ml of a phosphate buffer solution containing 1,000 Sumner units of commercial urease (obtained from Nakarai Chemical Co.) and gently shaken at 4° C. for 12 hours to effect immobilization of the enzyme. After completion of the immobilization, the immobilized enzyme was washed with 5 M sodium chloride solution, 0.1 M phosphate buffer solution (pH 6.7) and then distilled water. The activity of the immobilized enzyme was assayed by the colorimetric method of Van Slyke et al. (D. D. Van Slyke and R. M. Archibald J. Biol. Chem., 154 623 (1944)) and found to be 500 Sumner units.

EXAMPLE 12

2.0 Grams of the DEAE-pullulan gel having the same properties as those of the gel used in Example 5 were reacted with cyanuric chloride under the same conditions as in Example 8 and washed in a manner similar to that in Example 8 to obtain a s-triazinyl DEAE-pullulan gel. 400 Milligrams of the same β-galactosidase derived from *Asparagillus oryzae* as used in Example 7 was used to be immobilized on the above gel in the same manner as in Example 8. The immobilized amount was 120 mg per g of dry carrier and the specific activity of the immobilized enzyme was 2.2 μmoles/mg min., as assayed at 30° C. and pH 4.5 using 5% lactose solution as substrate solution.

EXAMPLE 13

2 Grams of a hydrophilic pullulan gel, 37 to 74μ in particle diameter in dry condition, having a water regain of 3.5 g/g, which had been prepared from pullulan of an average molecular weight of 100,000 by crosslinking with epichlorohydrin, was immersed in 25 ml of 1 N sodium hydroxide solution and stirred for 15 minutes at room temperature (about 20° C.). After removal of the excess alkali solution by filtration, the hydrophilic pullulan gel thus treated was immersed in 25 ml of dioxane and stirred for 5 minutes at room temperature. To the gel in dioxane, were added 20 ml of dioxane solution containing 4 g of cyanuric chloride and stirred vigorously at room temperature. After one minute, to the reaction mixture were added 25 ml of ice-cooled water followed quickly by 25 ml of acetic acid to terminate the reaction. After having been removed of the solvent by filtration, the resulting s-triazinyl hydrophilic gel was quickly washed with cold acetone and ice-cooled water and immediately subjected to the immobilization treatment. The immobilization treatment was carried out by adding the gel to a solution of 165 mg of Pronase E dissolved in 20 ml of phosphate buffer solution which had been kept at 4° C. and pH 8.0 and stirring the resulting mixture for 5 hours while keeping the pH at 8.0 by the addition of 0.2 N sodium hydroxide solution and controlling the temperature so as not to exceed 4° C. After 5 hours of reaction, the immobilized enzyme was separated by filtration and washed with 5 M sodium chloride solution, 0.1 M phosphate buffer solution (pH 6.0) and cold water until no protein had been detected in the washing. The washings were recovered. From the intensity of ultraviolet absorption of the recovered solution at 280 nm, the amount of immobilized enzyme was found to be 76 mg per g of dry gel. The specific activity of the immobilized enzyme thus obtained was assayed by means of a pH-stat using DL-lysine methyl ester as substrate at 30° C., pH 6.0, and a substrate concentration of 10% by weight and found to be 2.53 μmoles/mg.min., corresponding to 52% of the specific activity of the enzyme in the solution prior to immobilization.

EXAMPLE 14

Under the same conditions as in Example 13, 2 g of a hydrophilic gel, 37 to 74μ in diameter in dry condition, having a water regain of 2.7 g/g, which had been prepared from pullulan of an average molecular weight of 100,000 by crosslinking with epichlorohydrin, was reacted with cyanuric chloride and washed to prepare a s-triazinyl hydrophilic gel. The gel was added to 25 ml of 0.05 M phosphate buffer solution containing 60 mg of dissolved glucose isomerase (110 units/mg) obtained from *Streptomyces phaeochromogenes* and the immobilization and washing were carried out by the procedure as used in Example 13. The activity of the resulting immobilized enzyme was assayed by shaking the gel in 50 ml of phosphate buffer solution (0.05 M, pH 7.5, containing 0.005 M $Mg^{++}$ ion) containing 0.1 M of glucose, at 70° C. for one hour. It was found that the immobilized enzyme was 4,950 units. A portion of the immobilized enzyme, corresponding to 3,500 units, was packed in a jacketed column, 8 mm in diameter. While circulating hot water at 70° C. through the jacket, 3 M glucose solution (pH 7.5, containing 0.005 M $Mg^{++}$ion) was passed through the column at a space velocity of $3.5 \, hr^{-1}$. The amount of fructose in the effluent was determined by the method of cystein-carbazole-sulfuric acid and it was found that the conversion of glucose to fructose was 52%.

EXAMPLE 15

2 Grams of a hydrophilic gel having a particle diameter of 74 to 125μ in dry condition and a water region of 5.6 g/g, which had been prepared by the reaction of pullulan of an average molecular weight of 60,000 with epichlorohydrin, was immersed in 2 N sodium hydroxide solution and then carboxymethylated with monochloroacetic acid in a mixture of water and methanol. The carboxymethylated hydrophilic gel was converted to its methyl ester in methanol by using hydrogen chloride gas. The methyl ester was converted to hydrazide with hydrazine hydrate and further to azide with 3% sodium nitrite solution. The resulting azide was immediately immersed in 25 ml of phosphate buffer solution containing 1,000 Sumner units of commercial urease and gently shaken for 12 hours at 4° C. to effect immobilization of the enzyme. Thereafter, the immobilized enzyme was washed with 5 M sodium chloride solution, 0.1 M phosphate buffer solution (pH 6.7) and then distilled water. The activity of the immobilized enzyme thus prepared was assayed by the colorimetric method of Van Slyke et al. and found to be 480 Sumner units.

EXAMPLE 16

2 Grams of the same hydrophilic gel as used in Example 14 was immersed in 20 ml of dioxane solution containing 25 g of bromoacetic acid and gently stirred for 8 hours at room temperature. To the mixture was added slowly and dropwisely 17 ml of bromoacetyl bromide. After the addition, stirring was continued for further about 6 hours. After completion of the reaction, the reaction product was washed with an ice-cooled 0.1 M sodium carbonate solution and ice-cooled water to obtain bromoacetylated hydrophylic gel. The resulting gel was then immersed in 0.2 M phosphate buffer solution (pH 8.5) containing 100 mg of aminoacylase (10,000 units/g) and gently stirred for 18 hours at 5° C. to effect immobilization. The immobilized enzyme thus obtained was washed with phosphate buffer (pH 7.0) repeatedly and assayed for its activity. The assay was performed by determining the amount of L-methionine which was formed when the immobilized enzyme was allowed to react at 37° C. with 0.2 M solution (pH 7.0, containing $0.5 \times 10^{-4}$ M $CoCl_2$) of N-acetyl-DL-methionine used as substrate. It was found that the activity and immobilization of activity were 370 units and 37%, respectively. The activity assay was repeated 10 times. The retention of the activity on the tenth run was found to be 92% of the initial activity.

EXAMPLE 17

1.0 Grams of a hydrophilic gel having the same water regain and particle diameter as those of the gel used in Example 15 was immersed in 10 ml of 15% (W/V) titanium (IV) chloride solution and stirred well for 5 minutes. Thereafter, the gel was separated by filtration and washed with a large volume of water followed by acetate buffer solution (pH 5.0). The resulting hydrophilic gel-titanium derivative was immersed in 0.1 M succinate buffer solution (pH 5.0) containing 100 mg of invertase and stirred for 18 hours at 4° C. to effect immobilization of the enzyme. The immobilized enzyme was thoroughly washed with 0.5 M sodium chloride solution and 0.1 M succinate buffer solution. The activity of the immobilized enzyme thus prepared was found to be 720 units, as assayed at 55° C. by using a 1% sucrose solution in 0.1 M succinate buffer solution.

Note: One unit of the invertase activity corresponds to the amount of enzyme which liberates 1 μmole of glucose per minute at 55° C. and pH 5.0.

EXAMPLE 18

1.0 Gram of a hydrophilic gel having the same water regain and particle diameter as those of the gel used in Example 15 was immersed in 40 ml of water. After the addition of 1.0 g of cyanogen bromide, the mixture was stirred while keeping at 4° C. by cooling and pH 11.0 by dropwise addition of 5 N sodium hydroxide solution. Immediately after the pH had showed no further decrease, the gel was separated by filtration and quickly washed with 0.1 M borate buffer solution (pH 8.0). The hydrophilic gel thus activated with cyanogen bromide was transferred into 10 ml of 0.1 M borate buffer solution (pH 8.0) containing 80 mg of Pronase E and shaken with gentle reciprocate movement for 2 hours at room temperature to immobilize the pronase. In order to deactivate the unreacted active group, the resulting gel with immobilized pronase was washed with 10 times its volume of water and then immersed in 1.0 M ethanolamine solution (pH 8.0). After having been stirred for 2 hours at room temperature, the gel with immobilized enzyme was separated by filtration and repeatedly washed with 0.1 M acetate buffer solution (pH 4.0) containing 1 M sodium chloride, 0.1 M borate buffer solution (pH 8.0) containing 1 M sodium chloride, and cold water. The washings were recovered. From the intensity of ultraviolet absorption at 280 nm of the recovered solution, the amount of immobilized enzyme was found to be 33 mg per g of dry gel. The specific activity of the immobilized enzyme was assayed by means of a pH-stat using DL-lysine methyl ester as substrate at 40° C., pH 6.0, and a substrate concentration of 10% (W/V) and found to be 2.76 μmoles/mg.min., corresponding to 46% of the specific activity of the enzyme in the solution prior to immobilization.

What is claimed is:

1. An immobilized enzyme prepared by a process which comprises covalently bonding an enzyme on an enzyme-immobilizing carrier by utilizing the reactivity of hydroxyl groups in said enzyme-immobilizing carrier which is a hydrophilic pullulan gel in spherical bead form of 10 to 500μ in diameter having a water regain of 1 to 50 g/g which is obtained by crosslinking pullulan with epichlorohydrin.

2. An immobilized enzyme according to claim 1, wherein the hydrophilic pullulan gel is obtained by dispersing an aqueous pullulan solution containing an alkaline substance in a dispersion medium which is immiscible with said aqueous solution and contains a dispersion stabilizer to form a two-phase system and adding epichlorohydrin to the two-phase system to crosslink pullulan with epichlorohydrin.

3. An immobilized enzyme according to claims 1 or 2, wherein covalently bonding of the enzyme on the enzyme-immobilizing carrier is effected by attachment by means of a triazinyl derivative using cyanuric chloride, attachment through an azide linkage, attachment by means of diazo linkage, attachment by means of a monohalogenacetyl derivative or attachment by means of the reaction with a chloride of titanium.

4. An immobilized enzyme according to claims 1 or 2, wherein the molecular weight of the pullulan is $1 \times 10^4$ to $1 \times 10^6$.

5. An immobilized enzyme according to claim 1, wherein crosslinking of pullulan with epichlorohydrin is carried out at 10° to 70° C.

6. An immobilized enzyme according to claim 2, wherein the alkaline substance is sodium hydroxide, potassium hydroxide or calcium hydroxide.

7. An immobilized enzyme prepared by a process which comprises adsorbing an enzyme on an enzyme-immobilizing carrier by contacting an aqueous enzyme solution with said enzyme-immobilizing carrier which is an ionic pullulan gel in spherical bead form of 10 to 500μ in diameter having a water regain of 1 to 50 g/g which is obtained by reacting in the presence of an alkaline substance said hydrophilic pullulan gel in claims 1 or 2 with a compound represented by the formula, $$X_1-R-Z_1$$

wherein $X_1$ is a halogen atom or $$CH_2-CH-,\quad \underset{O}{\diagdown\diagup}$$

R is a linear alkyl group having 1 to 3 carbon atoms, which may have a hydroxyl group as substituent, and $Z_1$ is a carboxyl group, sulfonic acid group, $$-N\diagup^{R_1}_{\diagdown R_2},\quad -\overset{\oplus}{N}\diagup^{R_1}_{\diagdown R_3}^{-R_2}$$

(where $R_1$, $R_2$ and $R_3$ are each hydrogen, methyl group, ethyl group, hydroxyethyl group) or a salt of these compounds.

8. An immobilized enzyme prepared by a process which comprises covalently bonding an enzyme on an enzyme-immobilizing carrier by utilizing the reactivity of hydroxyl groups, primary amino group, secondary amino group or carboxyl group in said enzyme-immobilizing carrier which is an ionic pullulan gel in spherical bead form of 10 to 500μ in diameter having a water regain of 1 to 50 g/g which is obtained by reacting in the presence of an alkaline substance said hydrophilic pullulan gel in claims 1 or 2 with a compound represented by the formula, $$X_1-R-Z_1$$

wherein $X_1$ is a halogen atom or $$-N\diagup^{R_1}_{\diagdown R_2},\quad -\overset{\oplus}{N}\diagup^{R_1}_{\diagdown R_3}^{-R_2}$$

R is a linear alkyl group having 1 to 3 carbon atoms, which may have a hydroxyl group as substituent and $Z_1$ is a carboxyl group, sulfonic acid group, $$-N\diagup^{R_1}_{\diagdown R_2},\quad -\overset{\oplus}{N}\diagup^{R_1}_{\diagdown R_3}^{-R_2}$$

(wherein $R_1$, $R_2$ and $R_3$ are each hydrogen, methyl group, ethyl group, hydroxyethyl group) or a salt of these compounds.

9. An immobilized enzyme according to claim 7, wherein the preparation of the ionic pullulan gel by reacting said hydrophilic pullulan gel in claims 1 or 2 with the compound represented by the formula, $X_1-R-Z_1$, is carried out in an aqueous solvent at 5° to 100° C.

10. An immobilized enzyme according to claim 8, wherein the preparation of the ionic pullulan gel by reacting said hydrophilic pullulan gel in claims 1 or 2 with the compound represented by the formula, $X_1-R-Z_1$, is carried out in an aqueous solvent at 5° to 100° C.

11. An immobilized enzyme according to claim 7, wherein the alkaline substance is sodium hydroxide, potassium hydroxide or calcium hydroxide.

12. An immobilized enzyme according to claim 8, wherein the alkaline substance is sodium hydroxide, potassium hydroxide or calcium hydroxide.

13. An immobilized enzyme according to claim 7, wherein the compound represented by the formula, $X_1-R-Z_1$, is 2-dimethylaminoethyl chloride, 2-diethylaminoethyl chloride, 3-diethylamino-1,2-epoxypropane, γ-chloro-β-hydroxypropyltrimethylammonium chloride, β,γ-epoxypropyltriethylammonium chloride, 2-chloroethylamine, monochloroacetic acid, 2-bromoethanesulfonic acid or salts thereof.

14. An immobilized enzyme according to claim 8, wherein the compound represented by the formula, $X_1-R-Z_1$, is dimethylaminoethyl chloride, 2-diethylaminoethyl chloride, 3-diethylamino-1,2-epoxypropane, γ-chloro-β-hydroxypropyltrimethylammonium chloride, β,γ-epoxypropyltriethylammonium chloride, 2-chloroethylamine, monochloroacetic acid, 2-bromoethanesulfonic acid or salts thereof.

15. An immobilized enzyme according to claim 13, wherein the compound represented by the formula, $X_1-R-Z_1$, is 2-diethylaminoethyl chloride, γ-chloro-β-hydroxypropyltrimethylammonium chloride, β,γ-epoxypropyltriethylammonium chloride, monochloroacetic acid or salts thereof.

16. An immobilized enzyme according to claim 14, wherein the compound represented by the formula, $X_1-R-Z_1$, is 2-diethylaminoethyl chloride, γ-chloro-β-hydroxypropyltrimethylammonium chloride, β,γ-epoxypropyltriethylammonium chloride, monochloroacetic acid or salts thereof.

17. An immobilized enzyme according to claim 8, wherein covalently bonding of the enzyme on the enzyme-immobilizing carrier is effected by attachment by means of triazinyl derivative by use of cyanuric chloride, attachment through an azide linkage, attachment by means of diazo linkage, attachment by means of a monohalogenacetyl derivative, attachment by use of carbodiimide derivative or attachment by use of glutaraldehyde.

18. An immobilized enzyme according to claim 1, wherein said enzyme is trypsin, chymotrypsin, lipase, microbial protease, esterase, urease, bromelain, ribonuclease, deoxyribonuclease, penicillin amidase, aminoacylase, β-galactosidase, glucose isomelase, glucose oxidase, creatine kinase, papain, invertase, pepsin, β-amylase, isoamylase, maltase or uricase.

19. An immobilized enzyme according to claim 7, wherein said enzyme is trypsin, chymotrypsin, lipase, microbial protease, esterase, urease, bromelain, ribonuclease, deoxyribonuclease, penicillin amidase, aminoacylase, β-galactosidase, glucose isomelase, glucose oxidase, creatine kinase, papain, invertase, pepsin, β-amylase, isoamylase, maltase or uricase.

20. An immobilized enzyme according to claim 8, wherein said enzyme is trypsin, chymotrypsin, lipase, microbial protease, esterase, urease, bromelain, ribonuclease, deoxyribonuclease, penicillin amidase, aminocylase, β-galactosidase, glucose isomelase, glucose oxidase, creatine kinase, papain, invertase, pepsin, β-amylase, isoamylase, maltase or uricase.

21. A process for preparing an immobilized enzyme which comprises covalently bonding an enzyme on an enzyme-immobilizing carrier by utilizing the reactivity of hydroxyl groups in said enzyme-immobilizing carrier which is a hydrophilic pullulan gel in spherical bead form of 10 to 500μ in diameter having a water regain of 1 to 50 g/g which is obtained by crosslinking pullulan with epichlorohydrin.

22. A process for preparing an immobilized enzyme according to claim 21, wherein the hydrophilic pullulan gel is obtained by dispersing an aqueous pullulan solution containing an alkaline substance in a dispersion medium which is immiscible with said aqueous solution and contains a dispersion stabilizer to form a two-phase system and adding epichlorohydrin to the two-phase system to crosslink pullulan with epichlorohydrin.

23. A process for preparing an immobilized enzyme according to claims 21 or 22, wherein covalently bonding of the enzyme on the enzyme-immobilizing carrier is effected by attachment by means of a triazinyl derivative using cyanuric chloride, attachment through an azide linkage, attachment by means of diazo linkage, attachment by means of a monohalogenacetyl derivative or attachment by means of the reaction with a chloride of titanium.

24. A process for preparing an immobilized enzyme which comprises adsorbing an enzyme on an enzyme-immobilizing carrier by contacting an aqueous enzyme solution with said enzyme-immobilizing carrier which is an ionic pullulan gel in spherical bead form of 10 to 500μ in diameter having a water regain of 1 to 50 g/g which is obtained by reacting in the presence of an alkaline substance said hydrophilic pullulan gel in claims 1 or 2 with a compound represented by the formula, $$X_1-R-Z_1$$

wherein $X_1$ is a halogen atom or

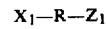

R is a linear alkyl group having 1 to 3 carbon atoms, which may have a hydroxyl group as substituent, and $Z_1$ is a carboxyl group, sulfonic acid group,

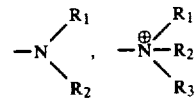

(where $R_1$, $R_2$ and $R_3$ are each hydrogen, methyl group, ethyl group, hydroxyethyl group) or a salt of these compounds.

25. A process for preparing an immobilized enzyme which comprises covalently bonding an enzyme on an enzyme-immobilizing carrier by utilizing the ractivity of hydroxyl groups, primary amino group, secondary amino group or carboxyl group in said enzyme-immobilizing carrier which is an ionic pullulan gel in spherical bead form of 10 to 500μ in diameter having a water regain of 1 to 50 g/g which is obtained by reacting in the presence of an alkaline substance said hydrophilic pullulan gel in claims 1 or 2 with a compound represented by the formula, $$X_1-R-Z_1$$

wherein $X_1$ is a halogen atom or

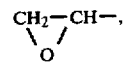

R is a linear alkyl group having to 1 to 3 carbon atoms, which may have a hydroxyl group as substituent and $Z_1$ is a carboxyl group, sulfonic acid group,

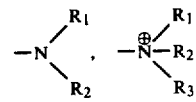

(where $R_1$, $R_2$ and $R_3$ are each hydrogen, methyl group, ethyl group, hydroxyethyl group) or a salt of these compounds.

* * * * *